(12) United States Patent
Liu et al.

(10) Patent No.: US 10,185,383 B2
(45) Date of Patent: Jan. 22, 2019

(54) POWER SUPPLY MANAGEABLE WEARABLE DEVICE AND POWER SUPPLY MANAGEMENT METHOD FOR A WEARABLE DEVICE

(71) Applicant: SHENZHEN GOODIX TECHNOLOGY CO., LTD., Shenzhen (CN)

(72) Inventors: Chang Liu, Shenzhen (CN); Wangwang Yang, Shenzhen (CN); Haixiang Wang, Shenzhen (CN)

(73) Assignee: SHENZHEN GOODIX TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 15/695,667

(22) Filed: Sep. 5, 2017

(65) Prior Publication Data

US 2018/0018010 A1 Jan. 18, 2018

Related U.S. Application Data

(63) Continuation of application No. PCT/CN2016/089775, filed on Jul. 12, 2016.

(51) Int. Cl.
*G06F 1/32* (2006.01)
*G16H 40/67* (2018.01)
(Continued)

(52) U.S. Cl.
CPC .......... *G06F 1/3228* (2013.01); *A61B 5/0022* (2013.01); *A61B 5/0205* (2013.01);
(Continued)

(58) Field of Classification Search
None
See application file for complete search history.

(56) References Cited

U.S. PATENT DOCUMENTS 5,891,042 A * 4/1999 Sham ................ A61B 5/02438
600/483
8,019,096 B2 * 9/2011 Sander ................ H04R 1/1041
381/122

(Continued)

FOREIGN PATENT DOCUMENTS

CN 105451115 A 3/2016

OTHER PUBLICATIONS

Chang et al, "Earphones with biological feature detection function, interaction system, and method." Google patent translation of CN105451115. Mar. 30, 2016.*

*Primary Examiner* — Curtis A Kuntz
*Assistant Examiner* — Qin Zhu

(57) ABSTRACT

A power supply manageable wearable device includes: a power management module connected to the microphone interface, a control module and a function module that are connected to the power management module respectively; wherein the control module monitors whether a user instruction includes a voice communication instruction; if the user instruction includes the voice communication instruction, the power management module is enabled to supply power to a microphone and output a first voltage to supply power to the control module; or otherwise, the power management module is enabled to cut off power supply to the microphone and output a second voltage to supply power to the control module and the function module, or output a first voltage to supply power to the control module and output a second voltage to supply power to the function module. The wearable device has the advantages of convenient use and low cost.

14 Claims, 13 Drawing Sheets

(51) Int. Cl.
*G06F 19/00* (2018.01)
*A61B 5/0205* (2006.01)
*A61B 5/00* (2006.01)
*G10L 25/21* (2013.01)
*G10L 25/87* (2013.01)
*G06F 1/16* (2006.01)
*G10L 15/22* (2006.01)
*G10L 25/78* (2013.01)

(52) U.S. Cl.
CPC .......... *A61B 5/6801* (2013.01); *A61B 5/7475* (2013.01); *G06F 1/163* (2013.01); *G06F 1/3287* (2013.01); *G06F 19/00* (2013.01); *G10L 25/21* (2013.01); *G10L 25/87* (2013.01); *G16H 40/67* (2018.01); *G10L 15/22* (2013.01); *G10L 25/78* (2013.01)

(56) References Cited

U.S. PATENT DOCUMENTS

| | | | | |
|---|---|---|---|---|
| 2014/0201639 A1* | 7/2014 | Savolainen | ............ | G10L 17/26 715/727 |
| 2014/0270260 A1* | 9/2014 | Goertz | ................ | G10L 25/84 381/110 |
| 2016/0049163 A1* | 2/2016 | Ioannidis | ............... | G10L 25/48 705/14.49 |
| 2016/0349831 A1* | 12/2016 | Lim | ..................... | G06F 1/3212 |

* cited by examiner

POWER SUPPLY MANAGEABLE WEARABLE DEVICE AND POWER SUPPLY MANAGEMENT METHOD FOR A WEARABLE DEVICE

CROSS-REFERENCE TO RELATED APPLICATIONS

This application is a continuation of International Patent Application No. PCT/CN2016/089775, with an international filing date of Jul. 12, 2016, which is hereby incorporated by reference in its entirety.

TECHNICAL FIELD

The present application relates to the technical field of wearable devices, and in particular, relates to a power supply manageable wearable device and a power supply management method for a wearable device.

BACKGROUND

With the popularity of smart wearable devices in the modern society, people are imposing higher and higher requirements on user experience of the smart wearable devices. The wearable devices may be in direct contact with human bodies or articles carried on the human bodies, and collect relevant physiological data of people. The wearable devices generally need to maintain the contact with people and keep normal operation state. Therefore, the wearable devices need to have a powerful battery life.

Users may supply power to the smart wearable devices by using independent power supplies. Although most of the wearable devices employs the ultra-low power consumption technology, relative to the quickly innovated wearable devices, development of the batteries of the wearable devices is slow, and the users still need to frequently charge the wearable devices to ensure sufficient battery power.

In addition, most wearable devices need to be charged using external chargers, and the users need to carry more devices, which is not convenient.

Therefore, it is a technical problem to be urgently solved in the related art as how to better implement power supplies for the wearable devices.

SUMMARY

In view of the above technical problem, the present application provides a power supply manageable wearable device, and a power supply management method for a wearable device, which wholly or partially solve the above technical problem.

According to one aspect of the present application, a power supply manageable wearable device is provided. A smart device supplies power for the wearable device via a microphone interface. The wearable device includes: a power management module connected to the microphone interface, a control module and a function module that are connected to the power management module respectively.

The control module monitors whether a user instruction includes a voice communication instruction.

If the user instruction includes the voice communication instruction, the power management module is enabled to supply power to a microphone and output a first voltage to supply power to the control module.

Otherwise, the power management module is enabled to cut off power supply to the microphone and output a second voltage to supply power to the control module and the function module, or output a first voltage to supply power to the control module and output a second voltage to supply power to the function module, the first voltage being less than the second voltage.

According to another aspect of the present application, a power supply management method for a wearable device is provided. A smart device supplies power to the wearable device via a microphone interface. The wearable device includes: a power management module connected to the microphone interface, a control module and a function module that are connected to the power management module respectively. The power supply management method includes:

monitoring whether a user instruction includes a voice communication instruction;

supplying power to a microphone, and outputting a first voltage to supply power to the control module if the user instruction includes the voice communication instruction; and otherwise, cutting off power supply to the microphone, outputting a second voltage to supply power to the control module and the function module, or outputting a first voltage supply power to the control module and outputting a second voltage to supply power to the function module, the first voltage being less than the second voltage.

With the power supply manageable wearable device and the power supply management method thereof according to the present application, power is supplied to the wearable device using a microphone interface in a smart device. In this way, power is supplied to the wearable device without affecting use of the microphone in the wearable device, the use is convenient and the cost is low.

The above description only summarizes the technical solutions of the present application. Specific embodiments of the present application are described hereinafter to better and clearer understand the technical solutions of the present application, to practice the technical solutions based on the disclosure of the specification and to make the above and other objectives, features and advantages of the present application more apparent and understandable.

BRIEF DESCRIPTION OF THE DRAWINGS

By reading the detailed description of preferred embodiments hereinafter, various other advantages and beneficial effects become clear and apparent for persons of ordinary skill in the art. The accompanying drawings are merely for illustrating the preferred embodiments, but shall not be construed as limiting the present application. In all the accompanying drawings, like reference signs denote like parts. In the drawings.

DETAILED DESCRIPTION

Some exemplary embodiments of the present application are hereinafter described in detail with reference to the accompanying drawings. Although the accompanying drawings illustrate the exemplary embodiments of the present application, it shall be understood that the present application may be practiced in various manners, and the present application shall not be limited by the embodiments illustrated herein. On the contrary, these embodiments are described herein only for the purpose of better understanding the present application, and may integrally convey the scope of the present application to a person skilled in the art.

Figure 1:
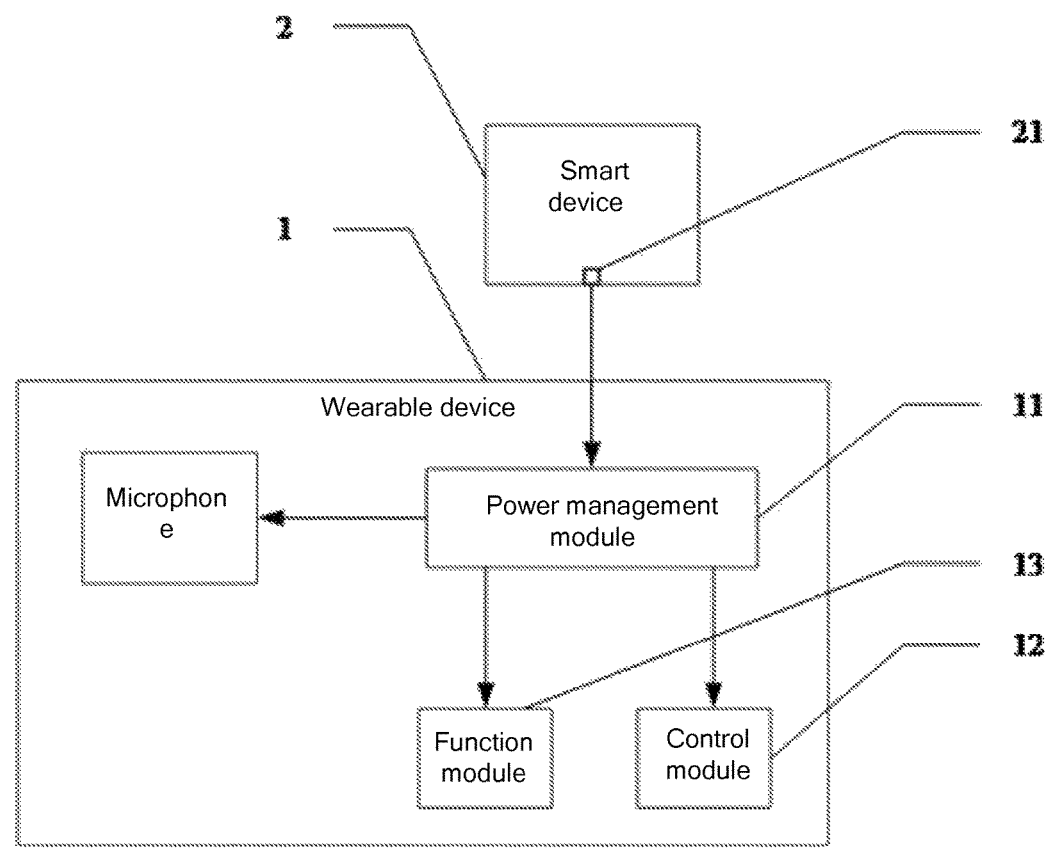
FIG. 1 is a schematic structural diagram of a power supply manageable wearable device according to one embodiment of the present application.

Referring to FIG. 1, one embodiment of the present application provides a power supply manageable wearable device 1. A smart device 2 supplies power to the wearable device 1 via a microphone interface 21. The wearable device includes: a power management module 11 connected to the microphone interface 21, a control module 12 and a function module 13 that are connected to the power management module 11 respectively.

Specifically, the smart device 2 receives a voice communication instruction via the microphone interface 21 and meanwhile the smart device 2 supplies power to the wearable device 1 via the microphone interface 21, and the microphone interface 21 is a multiplexed interface.

The control module 12 monitors whether a user instruction includes a voice communication instruction.

If the user instruction includes the voice communication instruction, the power management module 11 is enabled to supply power to a microphone and output a first voltage to supply power to the control module 12.

Otherwise, the power management module 11 is enabled to cut off power supply to the microphone and output a second voltage to supply power to the control module 12 and the function module 13, or output a first voltage to supply power to the control module 12 and output a second voltage to supply power to the function module 13, the first voltage being less than the second voltage.

Specifically, the function module 13 is configured to perform user biological feature detection, for example, heart rate detection, step counting, body temperature detection, blood oxygen detection and the like.

If the control module 12 monitors that the user instruction includes the voice communication instruction, that is, the microphone operates, the power management module 11 supplies power to the microphone, and only needs to provide the lower first voltage to the control module 12 for supplying power, such that normal operation of the microphone is ensured.

If the control module 12 monitors that the user instruction does not include the voice communication instruction, that is, the microphone does not operate, the power management module 11 outputs the second voltage to supply power to the control module 12 and the function module 13, or, outputs the first voltage to supply power to the control module 12 and the second voltage to supply power to the function module 13. The control module 12 constantly detects the user instruction, and the function module 13 performs user biological feature detection, for example, heart rate detection, step counting, body temperature detection, blood oxygen detection and the like.

Figure 2:
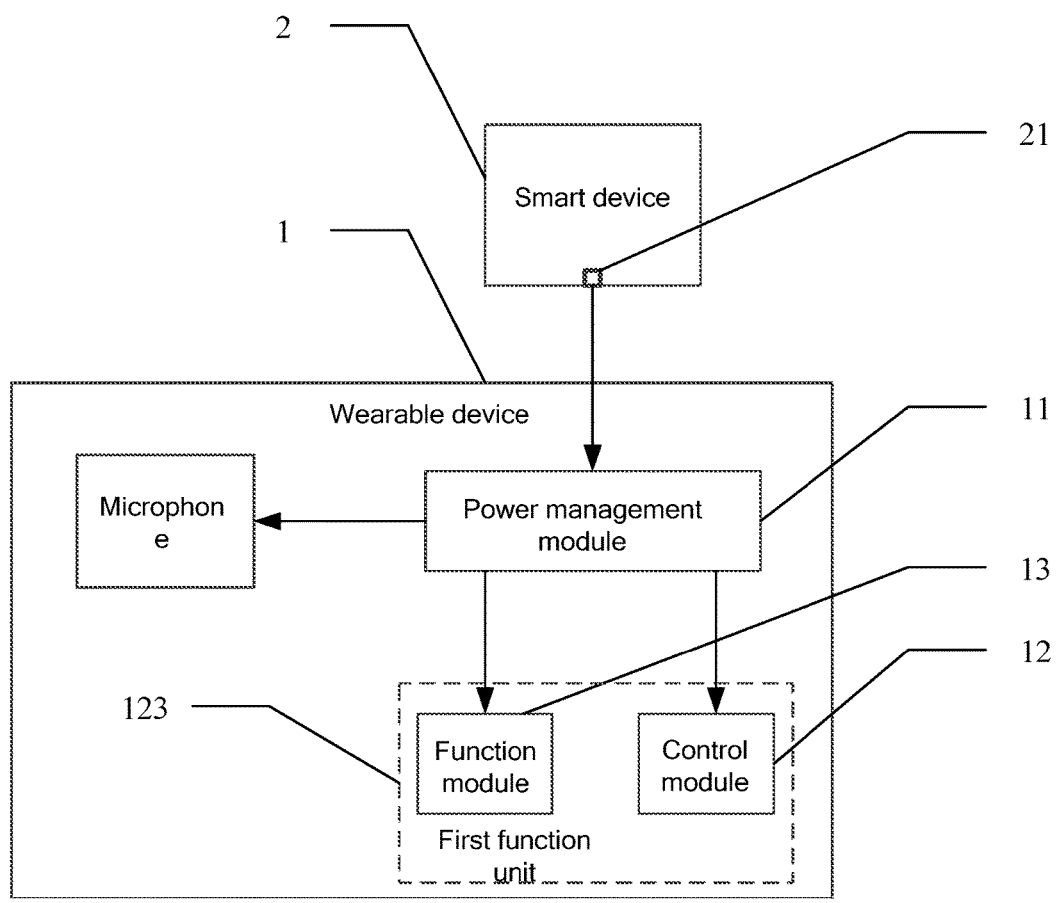
FIG. 2 is a schematic structural diagram of a power supply manageable wearable device according to another embodiment of the present application.

In another specific embodiment of the present application, referring to FIG. 2, the control module 12 and the function module 13 are integrated as a first function unit 123.

The first function unit 123 supports two operating modes. When the power management module 11 outputs a first operating voltage, the first function unit operates in a first operating mode, and the control module 12 in the first function unit only operates to monitor the user instruction sent by the smart device 2. When the power management module 11 outputs a second operating voltage, the first function unit operates in a second operating mode, the control module 12 and the function module 13 in the first function unit operate to monitor a user instruction for body feature monitoring and the like while monitoring the user instruction sent by the smart device 2.

The control module 12 and the function module 13 in this embodiment may be integrated as a first function unit 123, such that the design of the wearable device 1 is simpler.

Figure 3:
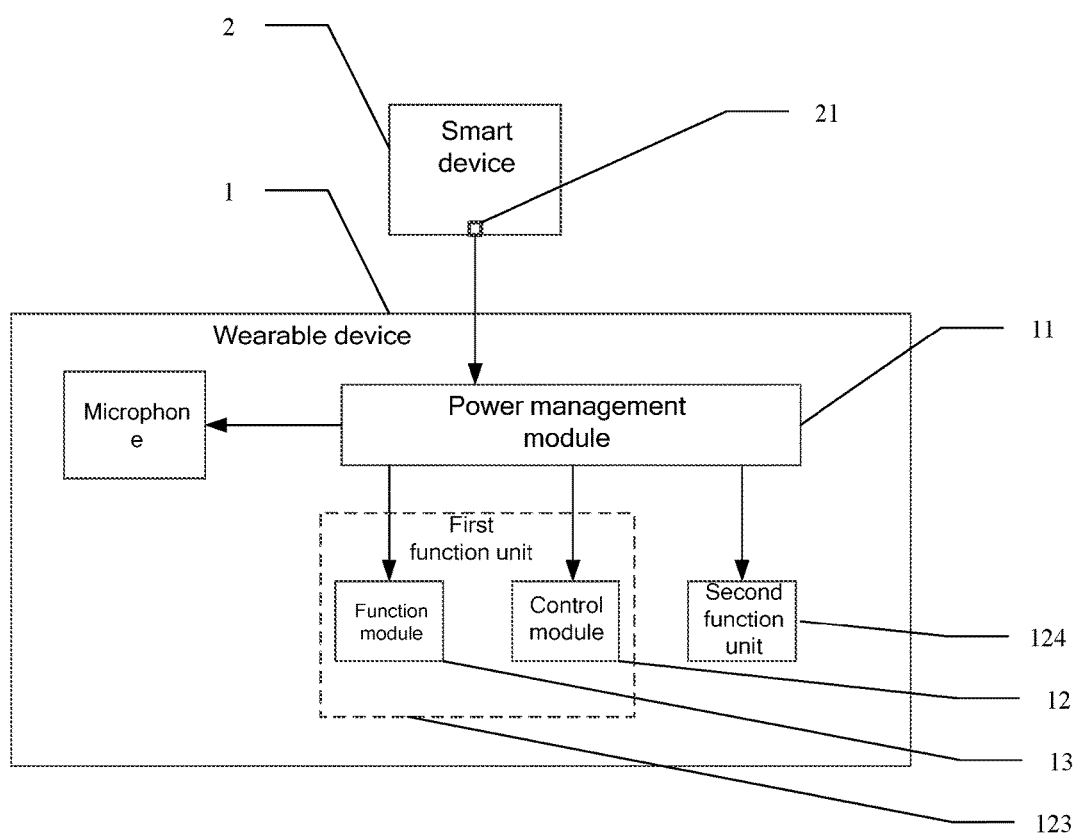
FIG. 3 is a schematic structural diagram of a power supply manageable wearable device according to still another embodiment of the present application.

In still another specific embodiment of the present application, referring to FIG. 3, the wearable device 1 further includes a second function unit 124.

When the power management module 11 outputs the first voltage, the control module 12 is configured to enable the second function unit 124 to stop operating.

When the power management module 11 outputs the second voltage, the control module 12 is configured to enable the second function unit 124 to operate.

Specifically, the second function unit 124 is configured to perform user biological feature detection, for example, heart rate detection, step counting, body temperature detection, blood oxygen detection and the like.

If the control module 12 monitors that the user instruction includes the voice communication instruction, that is, when the microphone operates, the power management module 11 supplies power to the microphone, and the second function unit 124 stops operating, such that normal operation of the microphone is ensured.

If the control module 12 monitors that the user instruction does not include the voice communication instruction, that is, the microphone does not operate, the power management module 11 outputs the second voltage to supply power to the second function unit 124. The second function unit 124 performs user biological feature detection, for example, heart rate detection, step counting, body temperature detection, blood oxygen detection and the like.

Figure 4:
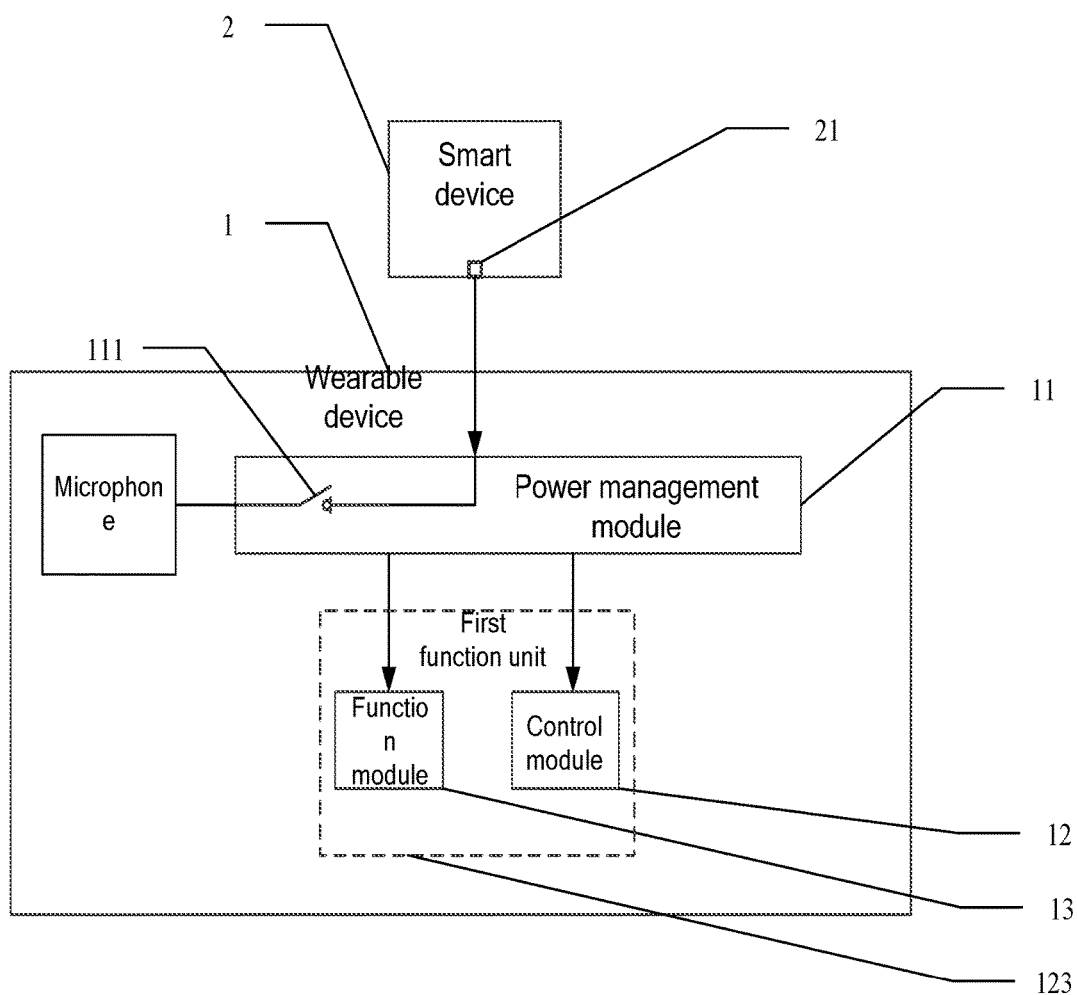
FIG. 4 is a schematic structural diagram of a power supply manageable wearable device according to yet still another embodiment of the present application.

In yet still another specific embodiment of the present application, referring to FIG. 4, the power management module 11 according to the present application further includes:

a first switch module 111, where if the control module 12 monitors that the user instruction includes the voice communication instruction, the first switch module 111 is configured to control the power management module 11 to supply power to the microphone, or otherwise, the first switch module 111 is configured to control the power management module 11 to cut off power supply to the microphone.

The control module 12 according to the present application selects, by means of switch-on or switch-off of the first switch module 111, whether to supply power to the microphone and the circuit design is simple, which facilitates operation and control.

Figure 5:
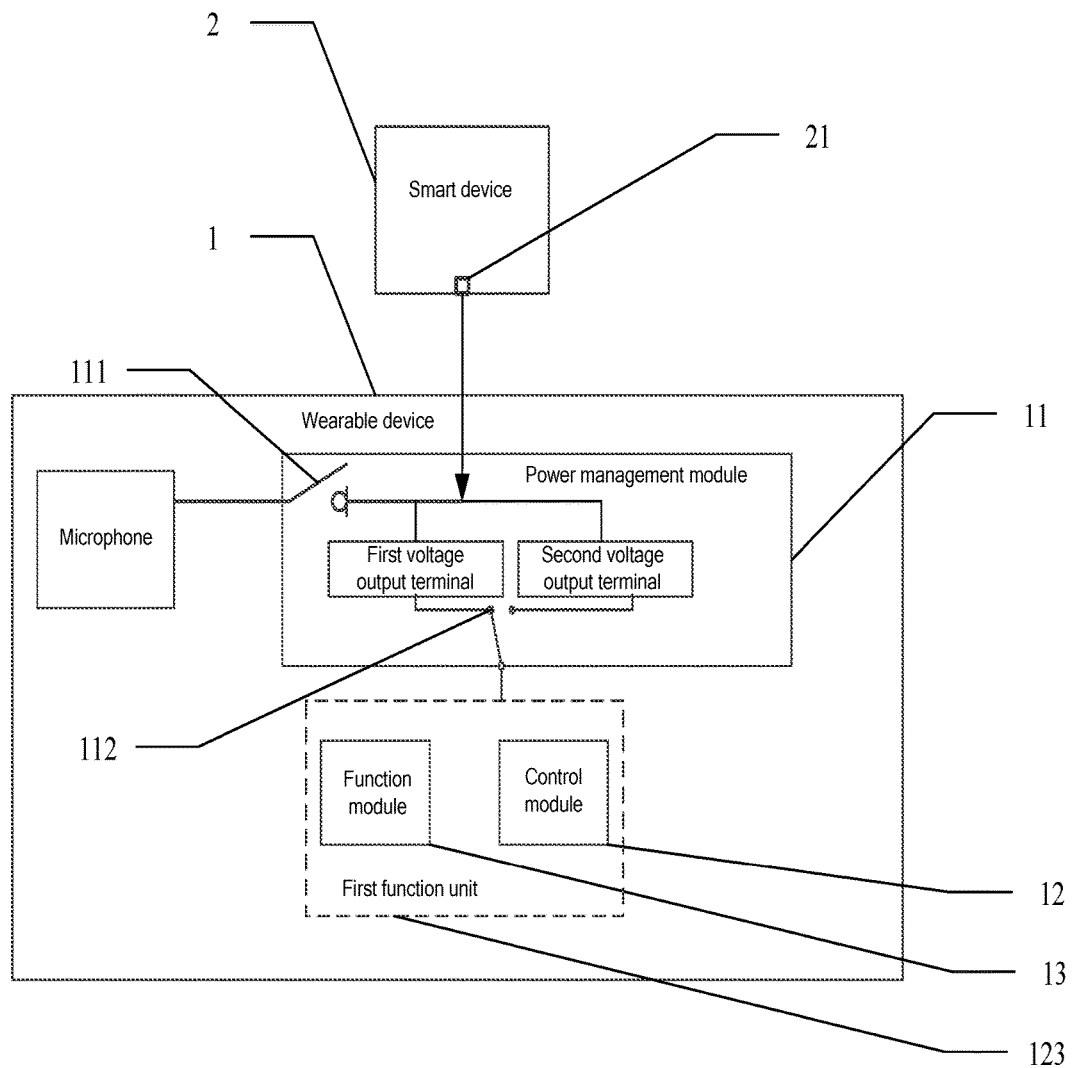
FIG. 5 is a schematic structural diagram of a power supply manageable wearable device according to yet still another embodiment of the present application.

In yet still another specific embodiment of the present application, referring to FIG. 5, the power management module 11 according to the present application further includes:

a second switch module 112, where if the control module 12 monitors that the user instruction includes the voice communication instruction, the second switch module 112 is configured to conduct a first voltage output terminal such that the power management module 11 outputs the first voltage to supply power to the control module 12, or otherwise, the second switch 112 is configured to conduct a second voltage output terminal such that the power management module 11 outputs a second voltage to supply power to the control module 12 and the function module 13.

The control module 12 according to the present application selects, by means of the conduction direction of the second switch module 112, to output the first voltage or the second voltage and the circuit design is simple, which facilitates operation and control.

Figure 6:
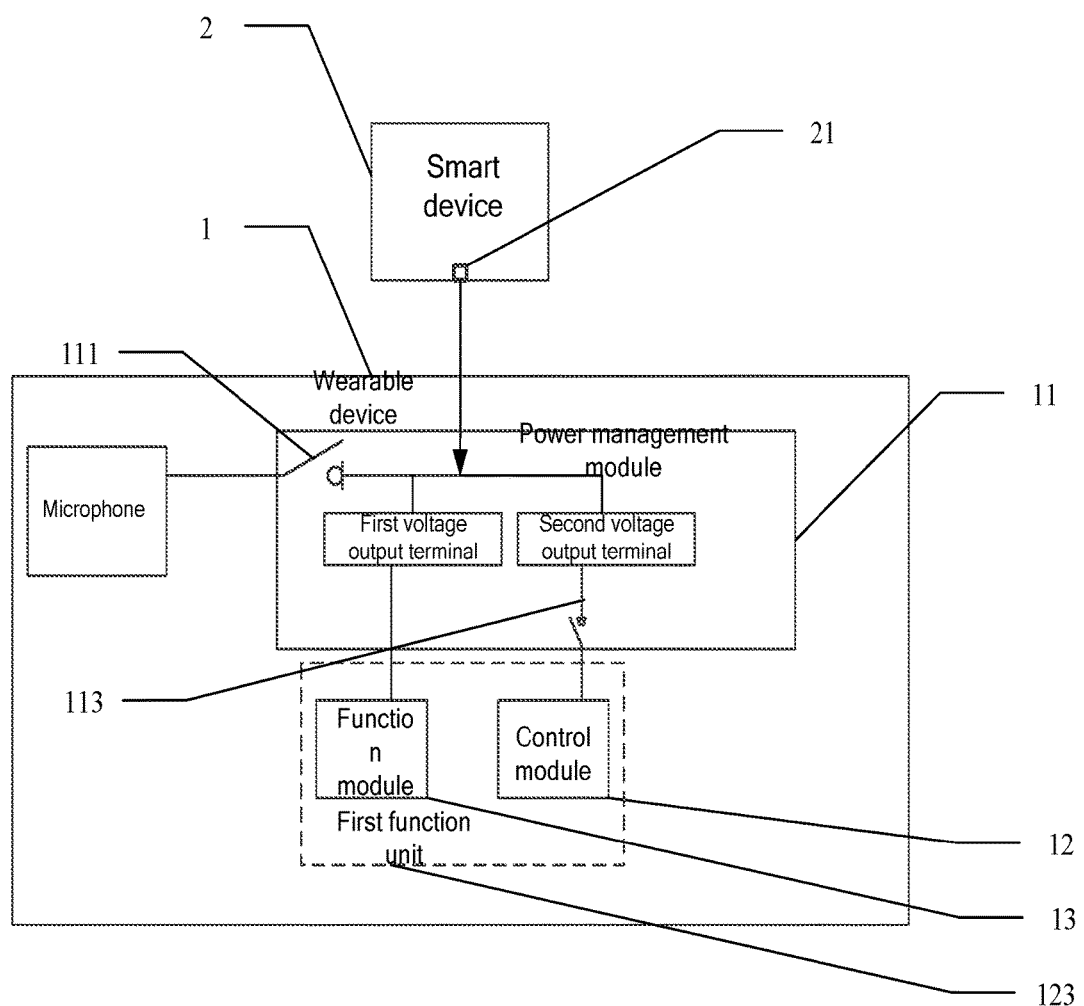
FIG. 6 is a schematic structural diagram of a power supply manageable wearable device according to yet still another embodiment of the present application.

In yet still another specific embodiment of the present application, referring to FIG. 6, the power management module 11 according to the present application further includes:

a third switch module 113, where if the control module 12 monitors that the user instruction includes the voice communication instruction, the third switch module 113 is configured to control the power management module 11 to cut off power supply to the function module 13, or otherwise, the third switch module 113 is configured to control the power management module 11 to output the second voltage to supply power to the function module 13.

The control module 12 according to the present application selects, by means of switch-on or switch-off of the third switch module 113, whether to output the second voltage to supply power to the function module 13 and the circuit design is simple, which facilitates operation and control.

Figure 7:
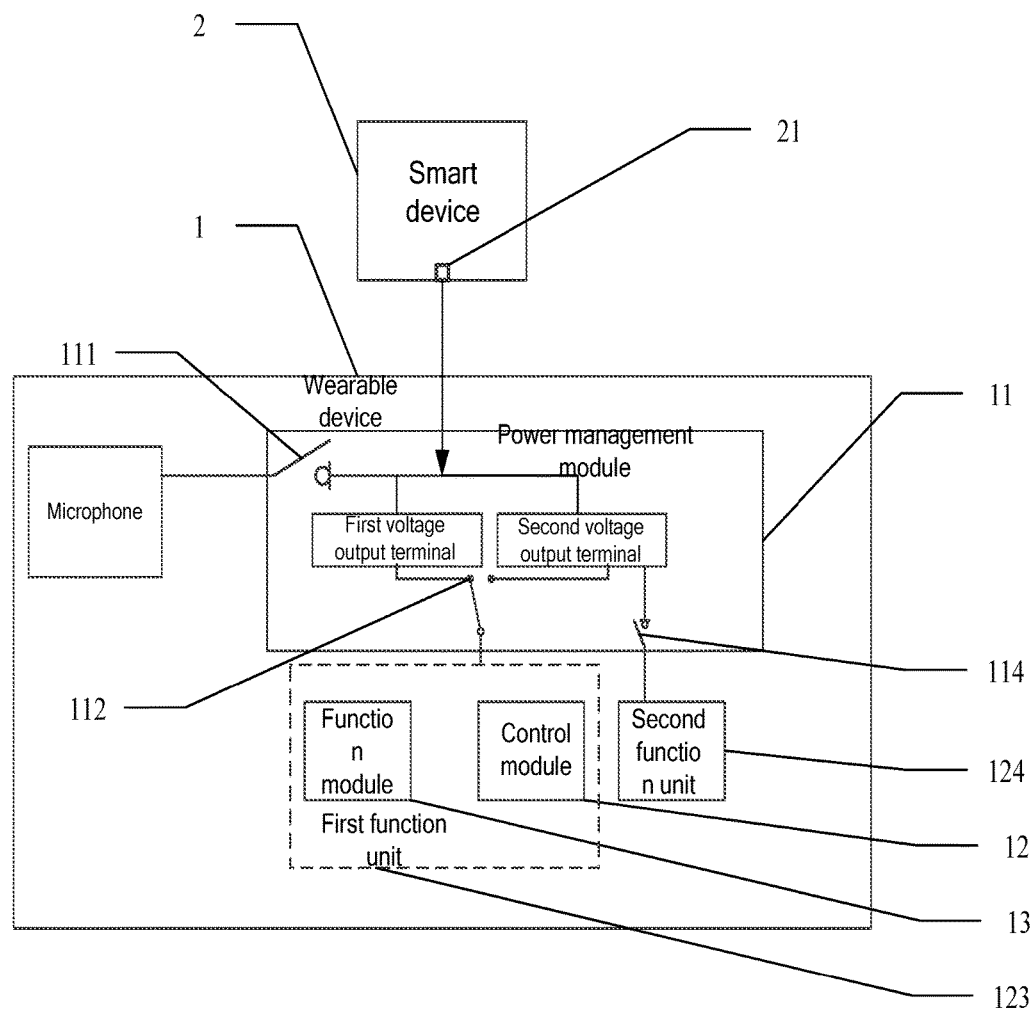
FIG. 7 is a schematic structural diagram of a power supply manageable wearable device according to yet still another embodiment of the present application.

In yet still another specific embodiment of the present application, referring to FIG. 7, the power management module 11 according to the present application further includes:

a fourth switch module 114, where if the control module 12 monitors that the user instruction includes the voice communication instruction, the fourth switch module 114 is configured to control the power management module 11 to cut off power supply to the second function unit 124, or otherwise, the fourth switch module 114 is configured to control the power management module 11 to output the second voltage to supply power to the second function unit 124.

The control module 12 according to the present application selects, by means of switch-on or switch-off the fourth switch module 114 whether to output the second voltage to supply power to the second function unit 124 and the circuit design is simple, which facilitates operation and control.

Figure 8:
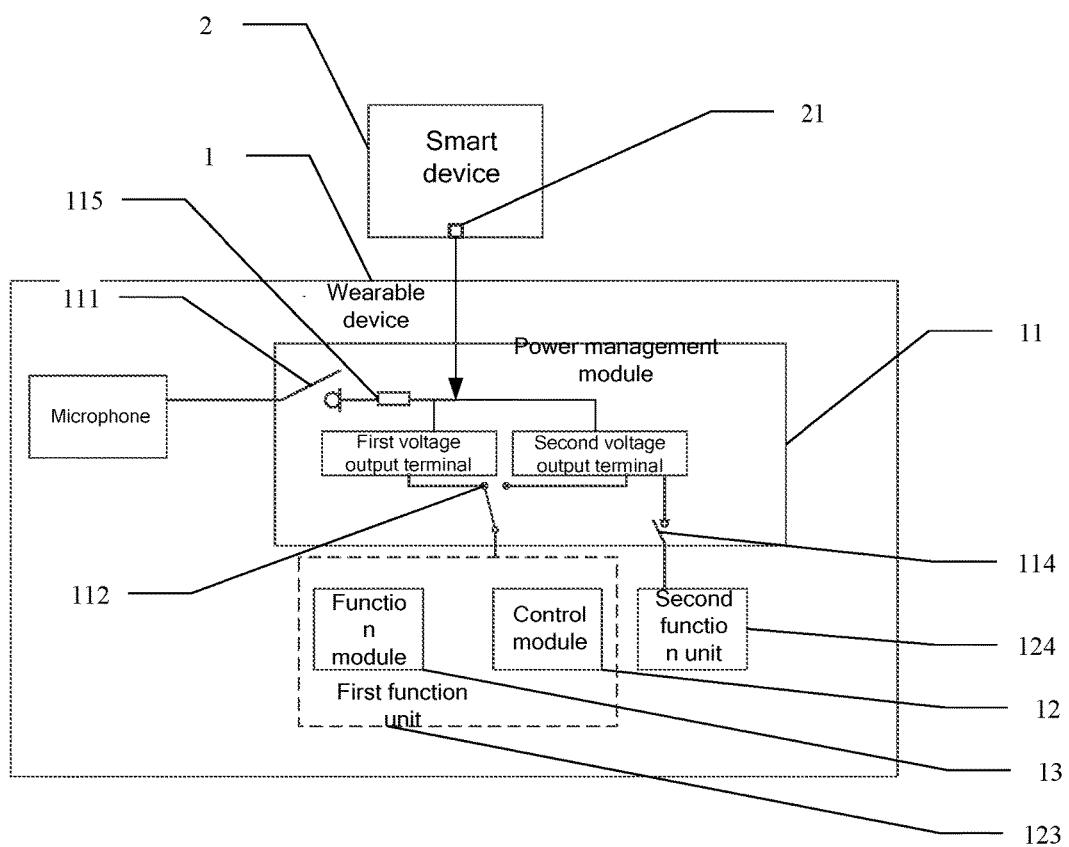
FIG. 8 is a schematic structural diagram of a power supply manageable wearable device according to yet still another embodiment of the present application.

In yet still another specific embodiment of the present application, referring to FIG. 8, the power management module 11 according to the present application further includes an isolating unit 115. If the control module 12 monitors that the user instruction includes the voice communication instruction, the isolating unit 115 is enabled to perform an isolation operation, or otherwise, the isolating unit 115 is made to be short-circuited.

Specifically, the isolating unit 115 may be an isolating resistor.

According to the present application, the isolating unit 115 isolates the power management module 11, the control module 12 and the function module 13 during voice communication, which prevents the power management module 11, the control module 12 and the function module 13 from causing interference to voice communication.

Figure 9:
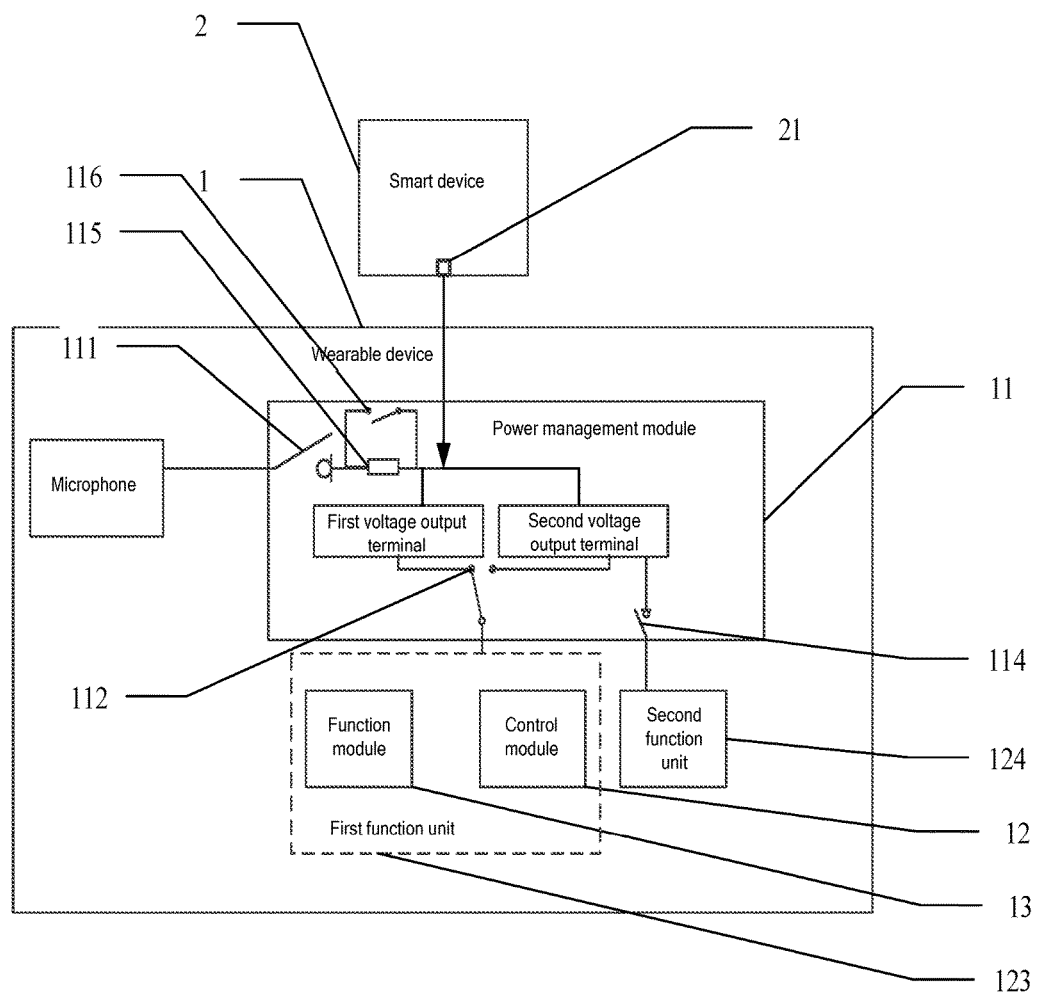
FIG. 9 is a schematic structural diagram of a power supply manageable wearable device according to yet still another embodiment of the present application.

In yet still another specific embodiment of the present application, referring to FIG. 9, the power management module 11 according to the present application further includes:

a fifth switch module 116, where if the control module 12 monitors that the user instruction includes the voice communication instruction, the fifth switch module 116 is configured to control the isolating unit 115 to perform the isolation operation, or otherwise, the fifth switch module 116 is configured to control the isolating unit 115 to be short-circuited.

According to the present application, whether the isolating unit 115 performs the isolation operation is determined by means of switch-off or switch-on of the fifth switch module 116, and the circuit design is simple, which facilitates operation and control.

Figure 10:
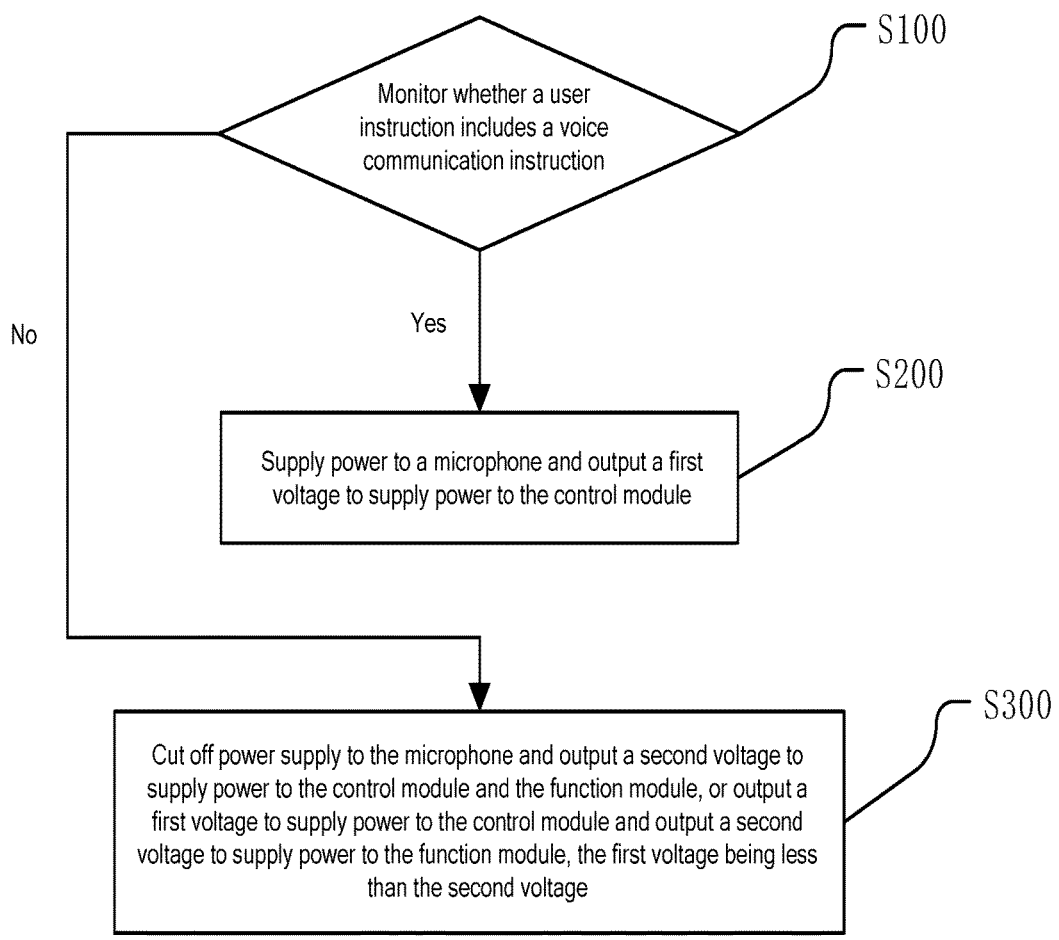
FIG. 10 is a schematic flowchart of a power supply management method for a wearable device according to one embodiment of the present application.

Referring to FIG. 10, one embodiment of the present application provides a power supply management method for a wearable device. A smart device supplies power to the wearable device via a microphone interface. The wearable device includes: a power management module connected to the microphone interface, a control module and a function module that are connected to the power management module respectively.

Specifically, the smart device receives a voice communication instruction via the microphone interface and meanwhile the smart device supplies power to the wearable device via the microphone interface, and the microphone interface is a multiplexed interface.

The power supply management method includes the following steps:

S100: monitoring whether a user instruction includes a voice communication instruction, performing step S200 if the user instruction includes the voice communication instruction, or otherwise, performing step S300;

S200: supplying power to a microphone, and outputting a first voltage to supply power to the control module if the user instruction includes the voice communication instruction; and S300: cutting off power supply to the microphone, outputting a second voltage to supply power to the control module and the function module, or outputting a first voltage supply power to the control module and outputting a second voltage to supply power to the function module, the first voltage being less than the second voltage.

Specifically, the function module is configured to perform user biological feature detection, for example, heart rate detection, step counting, body temperature detection, blood oxygen detection and the like.

If the control module monitors that the user instruction includes the voice communication instruction, that is, when the microphone operates, the power management module supplies power to the microphone, and only needs to provide the lower first voltage to the control module for supplying power, such that normal operation of the microphone is ensured.

If the control module monitors that the user instruction does not include the voice communication instruction, that is, the microphone does not operate, the power management module outputs the second voltage to supply power to the control module and the function module, or outputs the first voltage to supply power to the control module and the second voltage to supply power to the function module. The control module constantly detects the user instruction, and the function module performs user biological feature detection, for example, heart rate detection, step counting, body temperature detection, blood oxygen detection and the like.

Figure 11:
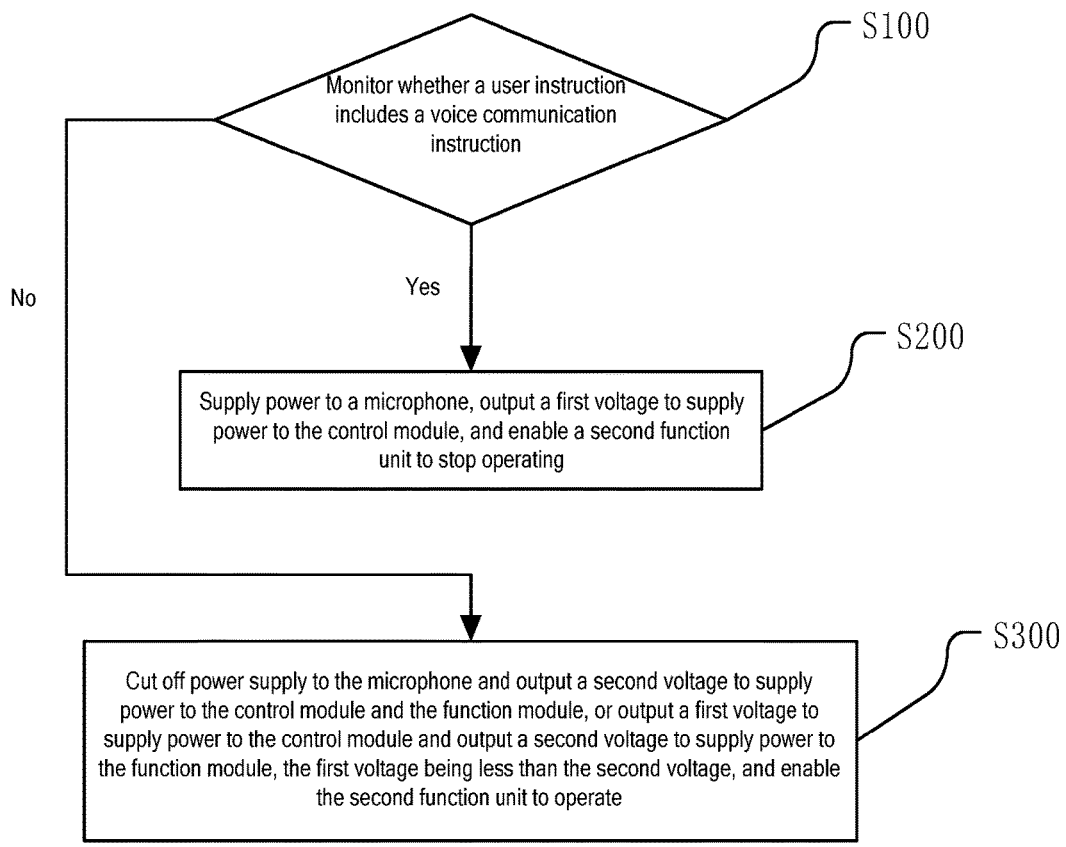
FIG. 11 is a schematic flowchart of a power supply management method for a wearable device according to another embodiment of the present application.

In another specific embodiment of the present application, referring to FIG. 11, step S200 further includes: enabling a second function unit to stop operating.

Step S300 further includes: outputting the second voltage to supply power to the second function unit.

Specifically, the second function unit is configured to perform user biological feature detection, for example, heart rate detection, step counting, body temperature detection, blood oxygen detection and the like.

If the control module monitors that the user instruction includes the voice communication instruction, that is, when the microphone operates, the power management module supplies power to the microphone, and the second function unit stops operating, such that normal operation of the microphone is ensured.

If the control module monitors that the user instruction does not include the voice communication instruction, that is, the microphone does not operate, the power management module outputs the second voltage to supply power to the second function unit. The second function unit is configured to perform user biological feature detection, for example, heart rate detection, step counting, body temperature detection, blood oxygen detection and the like.

Figure 12:
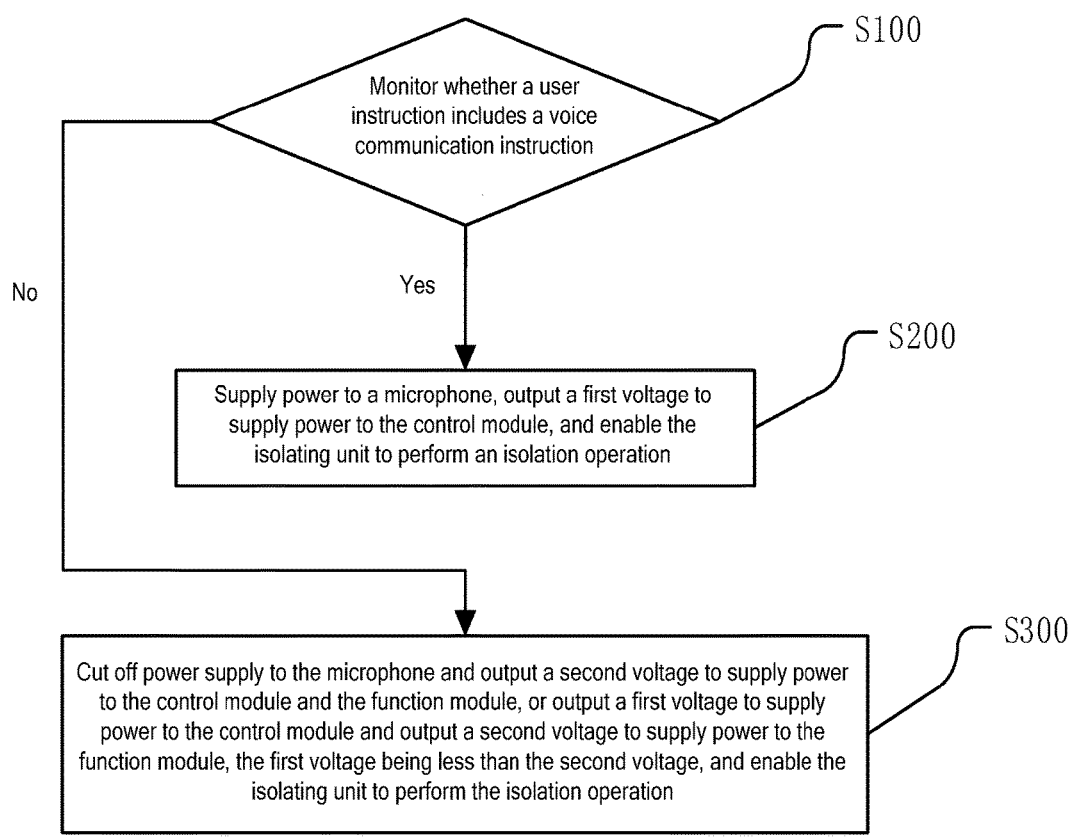
FIG. 12 is a schematic flowchart of a power supply management method for a wearable device according to still another embodiment of the present application.

In still another specific embodiment of the present application, referring to FIG. 12, step S200 further includes: enabling an isolating unit to perform an isolation operation.

Step S300 further includes: causing the isolating unit to be short-circuited.

Specifically, the isolating unit may be an isolating resistor.

According to the present application, the isolating unit isolates the power management module, the control module and the function module during voice communication, which prevents the power management module, the control module and the function module from causing interference to voice communication.

The following further describes an implementation of the present application with reference to a specific application scenario.

Figure 13:
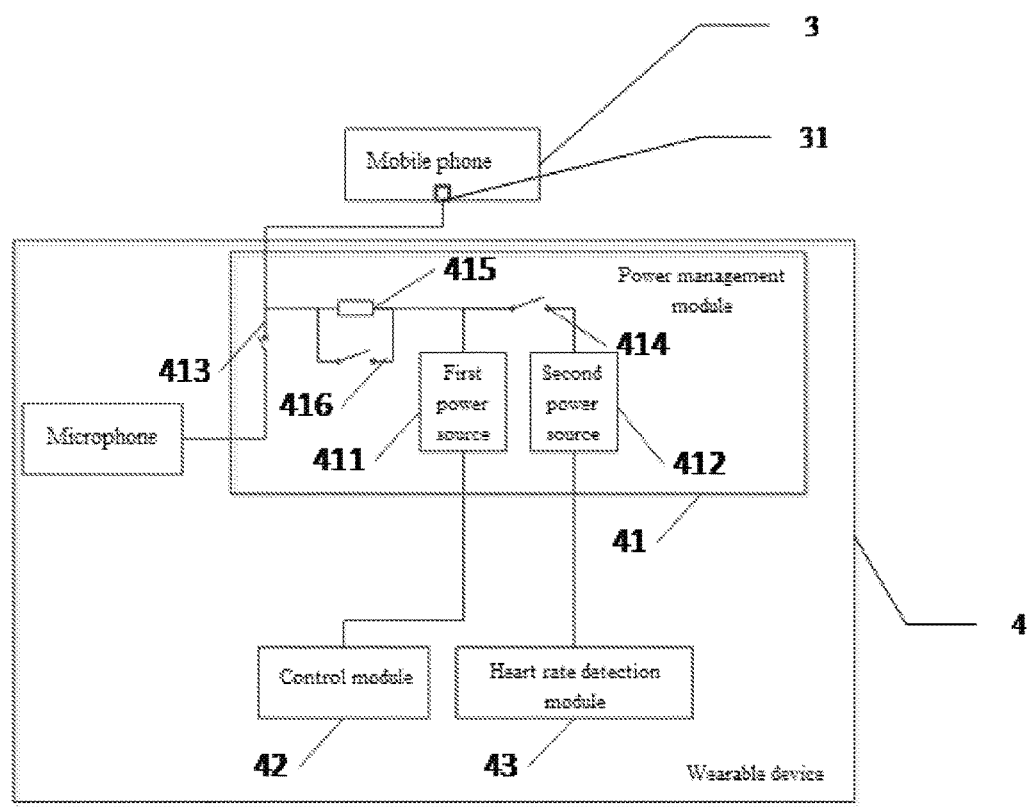
FIG. 13 is a schematic structural diagram of a specific application scenario according to the present application.

Referring to FIG. 13, the smart device is a mobile phone 3. The mobile phone supplies power to a wired microphone of a wearable device 4 for heart rate detection via a microphone interface 31 on the mobile phone, and the microphone interface 31 is also a microphone voice signal uploading interface. The microphone, as in the common wire-controlled headphone, implements the function of voice conversation and the like.

The wearable device 4 includes: a power management module 41, a control module 42 and a heart rate detection module 43.

The power management module 41 is configured to control the mobile phone 3 to supply power to the microphone, the control module 42 and the heart rate detection module 43 via the microphone interface 31.

The control module 42 is configured to detect a user instruction sent by the mobile phone 3, and control actions of the power management module 41.

The heart rate detection module 43 is configured to extract heart rate data of the user and upload the extracted heart rate data to the mobile phone 3.

The power management module 41 includes: a first power source 411, a second power source 412, a first switch module 413, a third switch module 414, a fourth switch module 416 and an isolating unit 415.

When the control module 42 detects, via the microphone interface 31 of the mobile phone 3, that the user instruction includes the voice communication instruction, the control module 42 controls the first switch module 413 to be configured to control the power management module 41 to supply power to the microphone, and to control the third switch module 414 to be configured to control the first power source 411 to output the first voltage to supply power the control module 42 and the heart rate detection module 43 stops operating.

When the control module 42 detects, via the microphone interface 31 of the mobile phone 3, that the user instruction does not include the voice communication instruction, the control module 42 controls the first switch module 413 to be configured to control the power management module 41 to cut off power supply to the microphone, and controls the third switch module 414 to be configured to control the first power source 411 to output the first voltage to supply power the control module 42 and the second power source 412 to output the second voltage to supply power to the heart rate detection module 43.

The fourth switch module 416 is configured to control if the user instruction includes the voice communication instruction, the isolating unit 415 to isolate signals of the microphone from other partial power supply. The isolating unit 415 may be, but not limited to, an isolating resistor. The fourth switch module 416 is configured to control if the user the user instruction does not include the voice communication instruction, the isolating unit 415 to be short-circuited.

According to the present application, on the premise of not affecting use of the microphone of a wired headphone, no additional charge is needed to supply power to the wearable device. The present application has the advantages of convenient use and low cost.

The algorithms and displays provided herein are not inherently related to any specific computer, virtual system or other device. Various general-purpose systems may also be used with the teachings herein. According to the above description, the structure required for constructing such systems is obvious. In addition, the present application is not directed to any specific programming language. It should be understood that the content of the present application described herein may be carried out utilizing various programming languages, and that the above description for a specific language is for the sake of disclosing preferred embodiments of the present application.

In the specification provided herein, a plenty of particular details are described. However, it can be appreciated that an embodiment of the present application may also be practiced without these particular details. In some embodiments, well known methods, structures and technologies are not illustrated in detail so as not to obscure the understanding of the specification.

Likewise, it shall be understood that, to streamline the present application and facilitate understanding of one or more of various aspects of the present application, in the above description of the exemplary embodiments of the present application, various features of the present application are sometimes incorporated in an individual embodiment, drawing or description thereof. However, the method according to the present application shall not be explained to embody the following intension: the present application seeking protection claims more features than those explicitly disclosed in each of the appended claims. To be more exact, as embodied in the appended claims, the inventive aspects lie in that fewer features than all the features embodied in an individual embodiment as described above. Therefore, the claims observing the specific embodiments are herein incorporated into the specific embodiments, and each claim may be deemed as an individual embodiment of the present application.

Those skilled in the art should understand that modules in the devices according to the embodiments may be adaptively modified and these modules may be configured in one or more devices different from the embodiments herein. Modules or units or components in the embodiments may be combined into a single module or unit or component, and additionally these modules, units or components may be practiced in a plurality of sub-modules, subunits or subcomponents. Besides that, such features and/or processes or at least some of the units are mutually exclusive, all the features disclosed in this specification (including the appended claims, abstract and accompanying drawings) and all the processes or units in such disclosed methods or devices may be combined in any way. Unless otherwise stated, each of the features disclosed in this specification (including the appended claims, abstract and accompanying drawings) may be replaced by a provided same, equivalent or similar substitution.

In addition, those skilled in the art shall understand that, although some embodiments described herein include some features included in other embodiments, rather than other features, a combination of the features in different embodiments signifies that the features are within the scope of the present application and different embodiments may be derived. For example, in the claims appended hereinafter, any one of the embodiments seeking protection may be practiced in any combination manner.

Embodiments of the individual components of the present application may be implemented in hardware, or in a software module running one or more processors, or in a combination thereof. It will be appreciated by those skilled in the art that, in practice, some or all of the functions of some or all of the components in the message prompting apparatus according to individual embodiments of the present application may be implemented using a microprocessor or a digital signal processor (DSP). The present application may also be implemented as an apparatus of a device program (e.g., a computer program and a computer program product) for performing a part or all of the method as described herein. Such a program implementing the present application may be stored on a computer readable medium, or may be stored in the form of one or more signals. Such a signal may be obtained by downloading it from an Internet website, or provided on a carrier signal, or provided in any other form.

Reference herein to "one embodiment", "an embodiment" or to "one or more embodiments" implies that a particular feature, structure, or characteristic described in connection with the embodiments is included in at least one embodiment of the present application. Further, it should be noted that instances of the phrase "in one embodiment" herein are not necessarily all referring to the same embodiment.

In the specification provided herein, a plenty of particular details are described. However, it can be appreciated that an embodiment of the present application may also be practiced without these particular details. In some embodiments, well known methods, structures and technologies are not illustrated in detail so as not to obscure the understanding of the specification.

It should be noted that the above embodiments illustrate rather than limit the present application, and those skilled in the art may design alternative embodiments without departing from the scope of the appended claims. In the claims, any reference sign placed between the parentheses shall not be construed as a limitation to a claim. The word "comprise" does not exclude the presence of a module or a step not listed in a claim. The word "a" or "an" used before a module does not exclude the presence of a plurality of such modules. The present application may be implemented by means of a hardware comprising several distinct modules and by means of a suitably programmed computer. In a unit claim enumerating several devices, several of the devices may be embodied by one and the same hardware item. Use of the words "first", "second", "third" and the like does not mean any ordering. Such words may be construed as naming.

What is claimed is:

1. A power supply manageable wearable device, wherein a smart device supplies power to the wearable device via a microphone interface, wherein the wearable device comprises:
   a power management module connected to the microphone interface;
   a function module connected to the power management module; and
   a control module connected to the power management module and configured to monitor whether a user instruction comprises a voice communication instruction; wherein
   if the user instruction comprises the voice communication instruction, the power management module is enabled to supply power to a microphone and output a first voltage to supply power to the control module;
   otherwise, the power management module is enabled to cut off power supply to the microphone and output a second voltage to supply power to the control module and the function module, or output the first voltage to supply power to the control module and output the second voltage to supply power to the function module, wherein the first voltage is lower than the second voltage, and
   the function module is configured to perform user biological feature detection.

2. The power supply manageable wearable device according to claim 1, wherein the control module and the function module are integrated as a first function unit.

3. The power supply manageable wearable device according to claim 2, further comprising a second function unit; wherein if the power management module outputs the first voltage, the control module is configured to enable the second function unit to stop operating; or if the power management module outputs the second voltage, the control module is configured to enable the second function unit to operate.

4. The power supply manageable wearable device according to claim 3, wherein the second function unit is configured to perform user biological feature detection.

5. The power supply manageable wearable device according to claim 3, further comprising:
a fourth switch module, wherein the fourth switch module is configured to control the power management module to cut off power supply to the second function unit if the control module monitors that the user instruction comprises the voice communication instruction, otherwise, the fourth switch module is configured to control the power managementre module to output the second voltage to supply power to the second function unit.

6. The power supply manageable wearable device according to claim 1, wherein the power management module further comprises:
a first switch module, wherein the first switch module is configured to control the power management module to supply power to the microphone if the control module monitors that the user instruction comprises the voice communication instruction, otherwise, the first switch is configured to control the power management module to cut off power supply to the microphone.

7. The power supply manageable wearable device according to claim 1, wherein the power management module further comprises:
a second switch module, wherein the second switch module is configured to conduct a first voltage output terminal such that the power management module outputs the first voltage to supply power to the control module if the control module monitors that the user instruction comprises the voice communication instruction, otherwise, the second switch module is configured to conduct a second voltage output terminal such that the power management module outputs a second voltage to supply power to the control module and the function module.

8. The power supply manageable wearable device according to claim 1, wherein the power management module further comprises:
a third switch module, wherein the third switch module is configured to control the power management module to cut off power supply to the function module if the control module monitors that the user instruction comprises the voice communication instruction, otherwise, the third switch module is configured to control the power management module to output the second voltage to supply power to the function module.

9. The power supply manageable wearable device according to claim 1, wherein the power management module comprises an isolating unit, the isolating unit is enabled to perform an isolation operation if the control module monitors that the user instruction comprises the voice communication instruction, otherwise, the isolating unit is short-circuited.

10. The power supply manageable wearable device according to claim 9, further comprising:
a fifth switch module, wherein the fifth switch module is configured to control the isolating unit to perform the isolation operation if the control module monitors that the user instruction comprises the voice communication instruction, otherwise, the fifth switch module is configured to control the isolating unit to be short-circuited.

11. A power supply management method for a wearable device, wherein a smart device supplies power to the wearable device via a microphone interface, wherein the wearable device comprises a power management module connected to the microphone interface, a control module connected to the power management module and configured to monitor whether a user instruction comprises a voice communication instruction and a function module that are connected to the power management module and configured to perform user biological feature detection respectively; the method comprising:
S100: monitoring whether a user instruction comprises a voice communication instruction, performing step S200 if the user instruction comprises the voice communication instruction, otherwise, performing step S300;
S200: supplying power to a microphone, and outputting a first voltage to supply power to the control module;
S300: cutting off power supply to the microphone; and outputting a second voltage to supply power to the control module and the function module; or
outputting the first voltage to supply power to the control module and outputting the second voltage to supply power to the function module,
wherein the first voltage is less than the second voltage.

12. The power supply management method for a wearable device according to claim 11, wherein
step S200 comprises enabling a second function unit to stop operating; and
step S300 comprises outputting the second voltage to supply power to the second function unit.

13. The power supply management method for a wearable device according to claim 11, wherein
step S200 comprises enabling an isolating unit to perform an isolation operation; and
step S300 comprises causing the isolating unit to be short-circuited.

14. The power supply management method for a wearable device according to claim 12, wherein
step S200 comprises enabling an isolating unit to perform an isolation operation; and
step S300 comprises causing the isolating unit to be short-circuited.

* * * * *